(12) United States Patent
Stierstorfer

(10) Patent No.: US 11,006,891 B2
(45) Date of Patent: May 18, 2021

(54) IBS RELATED TESTING AND TREATMENT

(71) Applicant: IBS Centers for Advanced Food Allergy Testing, LLC, Philadelphia, PA (US)

(72) Inventor: Michael Stierstorfer, Philadelphia, PA (US)

(73) Assignee: IBS CENTERS FOR ADVANCED FOOD ALLERGY TESTING, LLC, Philadelphia, PA (US)

( * ) Notice: Subject to any disclaimer, the term of this patent is extended or adjusted under 35 U.S.C. 154(b) by 559 days.

(21) Appl. No.: 15/448,543

(22) Filed: Mar. 2, 2017

(65) Prior Publication Data

US 2017/0196498 A1    Jul. 13, 2017

Related U.S. Application Data

(63) Continuation of application No. 12/796,960, filed on Jun. 9, 2010, now abandoned.

(51) Int. Cl.
*A61B 5/00*    (2006.01)
*A61B 10/00*   (2006.01)

(52) U.S. Cl.
CPC ............ *A61B 5/411* (2013.01); *A61B 5/4255* (2013.01); *A61B 5/445* (2013.01); *A61B 5/6833* (2013.01); *A61B 10/0035* (2013.01)

(58) Field of Classification Search
CPC .................................................. A61B 10/0035
See application file for complete search history.

(56) References Cited

U.S. PATENT DOCUMENTS

| | | | | |
|---|---|---|---|---|
| 4,543,964 A | * | 10/1985 | Breneman | A61B 5/411 |
| | | | | 600/556 |
| 2002/0106691 A1 | * | 8/2002 | Bryant | G01N 33/531 |
| | | | | 435/7.1 |
| 2006/0013773 A1 | * | 1/2006 | Power | G01N 33/6854 |
| | | | | 424/9.81 |
| 2007/0122840 A1 | * | 5/2007 | Cousins | G01N 33/543 |
| | | | | 435/7.1 |
| 2010/0022910 A1 | * | 1/2010 | Lane | A61B 5/0059 |
| | | | | 600/556 |

OTHER PUBLICATIONS

Alpha-Tocopherol; 2008; http://contactallergy.com/contact_allergy_008.htm 2002/0106691 A1 2006/0013773 A1.*
Dormer Laboratories Inc; Mar. 24, 2009; www.dormer.com; various pages (see attached).*
Contact Allergen Database; 2008; http://contactallergy.com/.*
Block, Eric; Garlic and Other Alliums: The Lore and The Science; May 28, 2010; Royal Society of Chemistry; 1st Edition, p. 288.*
ABC Action News—Local Doctor Helping Uncover Hidden Food Allergies.
AGA Technical Review on Irritable Bowel Syndrome, American Gastroenterological Association Clinical Practice Committee, 2002.
Amazon.com—You may not Have Irritable Bowel Syndrome . . . .
Dematology News—Skin patch testing pinpoints dietary triggers of IBS.
Enteragam.com—Clinical Case Studies Series—Patients With Chronic Diarrhea and Loose Stools.
Feldman, M. et al, Gastrointestinal and Liver Disease 2002-5-8-16-2, Read, N. Irritable Bowel Syndrome, Chapter 91.
Food alergy in irritable bowel syndrome, new facts and old fallacies, Isolauri, E. et al., www.gutjnl.com, 2004.
Food intolerance and theirritable bowel syndrome, R. Nanda, gut.bjm.com.
Is there a role of food allergy in irritable bowel syndrome and functional dyspepsia—a functional review, Park, M. et al., Neurogastroenterol Motil (2006).
Mertz, Howard R., Irritable Bowel Syndrome, N Engl J Med 2003;349-2136-46.
R. Spiller et al., Guidelines on the irritable bowel syndrome—mechanisms and practical management, Gut 2007; 56;1770-1798.
The irritable bowel syndrome Review and a graduated multicomponent treatment approach, Drossman, Douglas et al., Anals of Internal Medicine, Jul. 1992.
The Irritable Bowel Syndrome, Horwitz, Brenda et al., NEJM vol. 344, No. 24, Jun. 14, 2001.
The-Irritable-Bowel-Syndrome-Review-and-a-Graduated-Multicomponent-Treatment-Approach.
Type 1, 2, 3 & 4 Hypersensitivity—Stomp on Step 1.
Yamada, T. et al., Textbook of Gastroenterology 2003-5-8-16-4.
Zwetchkenbaum J., The irritable bowel syndrome and food hypersensitivity.

* cited by examiner

*Primary Examiner* — Devin B Henson
*Assistant Examiner* — H. Q. Nguyen
(74) *Attorney, Agent, or Firm* — Medler Ferro Woodhouse & Mills PLLC

(57) ABSTRACT

Methods and items useful at least therein are provided for IBS related testing and treatment. Disclosed is a patch useful in determining if one or more test materials can cause allergic contact dermatitis in a patient. A kit containing information on use and that may include such a patch and/or test material(s) is also disclosed. A method of IBS related testing including performing skin patch testing on a patient presenting IBS symptoms using at least one test material that can cause allergic contact dermatitis is provided. A method for the treatment of IBS which includes limiting the intake by a patient presenting IBS symptoms of at least one material that gives a positive skin patch test result in the patient is also disclosed.

18 Claims, No Drawings

IBS RELATED TESTING AND TREATMENT

CROSS-REFERENCE TO RELATED APPLICATION

This application is a continuation application of and claims benefit to U.S. application Ser. No. 12/796,960, filed Jun. 9, 2010, which is incorporated by reference herein.

FIELD OF THE INVENTION

This generally relates to methods and items for irritable bowel syndrome (IBS) related testing and treatment, and more particularly to IBS related patch testing.

BACKGROUND

IBS is a chronic disorder of the bowel. Its primary symptoms are abdominal pain or discomfort in association with frequent diarrhea or constipation or a change in bowel habits. There may be urgency for bowel movements, a feeling of incomplete evacuation, bloating or abdominal distention. Diarrhea or constipation may predominate, or they may alternate. The exact cause of IBS is currently considered unknown.

There is presently no cure for IBS. Treatments such as change in diet, medication and/or psychotherapy attempt to relieve symptoms, but they are not always very successful.

There are four commonly recognized types of immune reactions or hypersensitivities to foods and other materials, Gell-Coombs Types 1, 2, 3 and 4. Type 1 is characterized by the involvement of IgE antibodies produced in response to a particular material; typically testing here is by injecting or pricking the skin with the suspected allergen. A reaction is indicated if redness or swelling appears at the injection or prick test site.

Types 2 and 3 are characterized by the involvement of IgG, IgM, and some special IgE antibodies. Intradermal testing often fails to produce a reliable immune response in the skin. An elimination diet may be used here instead to detect the suspected material.

The Type 4 reaction involves sensitized lymphocytes or T-cells which respond to a specific material and which are believed to be at least as specific as an antibody to the material producing the immune response. Skin patch testing where one or more possible allergens are brought into contact with the surface of the skin may be used here. This reaction is seen as an allergic contact dermatitis, usually manifesting as a red macule(s), papule(s), plaque(s), vesicle(s) and/or bulla(e) at the patch test site.

U.S. Pat. Nos. 4,543,964 and 4,818,707 to Breneman disclose a device for the detecting of an individual's Gell-Coombs Types 1, 2, 3 and 4 immune response reactions to edible substances that include a mixture of an edible substance and a solution of non-toxic aprotic solvents, such as DMSO and water. The solution acts as a carrier transporting the test substance beneath the skin. The device holds the mixture against the skin and prevents evaporation of the solution. An associated method disclosed includes the preparation of a plurality of mixtures of different edible substances and a solution of a non-toxic aprotic solvent, the application of the mixture to the skin of the individual and the holding of the mixture on the skin for a predetermined period of time. The mixture is subsequently removed, and the site is inspected to determine whether a Type 1, 2, 3 or 4 Gell-Coombs immune response reaction has occurred. Control sites containing the solution only and a control site containing a food substance which causes the skin to fluoresce upon exposure to an ultraviolet light may also be used. Fluorescence indicates whether mixtures have been in sufficient contact with the skin for the required period of time. Several test foods are disclosed, including garlic and onion, but none appear emphasized alone nor are any combinations specified; these patents do not disclose links between allergies to foods or other materials and IBS. Contrary to Brenneman's statements, it is well known that skin patch testing is only used for Type 4 allergic reactions exclusively, and is not used for Type 1-3 allergic reactions. Type 4 reactions may also be referred to as delayed-type hypersensitivity allergic reactions. It is also well known that there are two arms of the immune system, the humoral arm and the cell-mediated arm. The humoral arm encompasses Type 1, 2 and 3 allergies, and the allergic mechanisms for all three of these allergies rely upon antibodies. The cell-mediated arm is limited to Type 4 allergies and relies upon white blood cells called lymphocytes. Testing is thus unique and distinctive for each of these allergy types.

It is estimated that 60-70% of individuals with IBS report that foods cause or aggravate their symptoms. Some believe that an allergic reaction may be involved. Currently, most attention regarding foods and allergy focuses on IgE-mediated (type 1 hypersensitivity) mechanisms.

There is a well-described gastrointestinal disease of infants and young children, food protein-induced enterocolitis, which is felt to be induced by a non-IgE mechanism. Skin patch testing is the only diagnostic testing available for this disease; compared to skin prick testing for diagnosis of IgE-mediated food allergies, patch testing is more specific, although somewhat less sensitive.

Many foods are known to cause allergic contact dermatitis (type 4 hypersensitivity); this is a non-IgE mediated reaction. Of these foods, many are very common in the average diet in the United States as well as in other countries.

The current standard of care in evaluation of individuals with symptoms suggestive of IBS does not include skin patch testing. There is currently no food patch test series targeting evaluation of IBS. Skin patch testing is typically in the realm of the medical specialty of dermatology; IBS is typically within the realm of the medical specialty of gastroenterology. Dermatologists are not trained in and do not typically address IBS issues, and gastroenterologists are not trained in and do not typically use patch testing in their work. These are two different fields of medicine.

IBS is a chronic illness and can dramatically reduce quality of life. Its sufferers have increased medical costs and work absenteeism. It is estimated that 15% of the U.S. population has IBS with similarly high and even higher rates reported for other countries. This high prevalence of IBS produces a very high cost to society. There is a need for new methods and items at least useful therein for IBS related testing and treatment.

SUMMARY

Methods and items that are useful at least therein are provided in accordance with the present invention for IBS related testing and treatment.

In accordance with the present invention, a patch for IBS related testing is provided that is attachable to skin and comprises one or more test materials, with the patch constructed such that at least one test material, selected from the group consisting of substances that can cause allergic contact dermatitis, may be brought into contact with skin to which the patch may be attached. Useful test materials may include garlic, an oleoresin fraction of garlic, diallyl disulfide, allylpropyl disulfide, allicin and/or others.

Consistent with the present invention, a kit is provided for IBS related testing comprising information on the use of the kit or direction to such information, the information comprising indication of at least a possible link between allergic contact dermatitis or at least one material that can cause allergic contact dermatitis and IBS. Other items such as a patch and/or at least one test material may be included as well.

Additionally, in accordance with the present invention, a method is provided for IBS related testing comprising performing skin patch testing on a patient presenting IBS symptoms using at least one test material that can cause allergic contact dermatitis. This method may further comprise other step(s) such as limiting the intake by the patient of at least one material that gives a positive skin patch test result in the patient.

Another method consistent with the present invention and provided is for the treatment of IBS comprising limiting the intake by a patient presenting IBS symptoms of at least one material that gives a positive skin patch test result in the patient.

DETAILED DESCRIPTION

Many foods, food additives and/or other materials are known to cause allergic contact dermatitis (type 4 hypersensitivity) of the skin. It is believed that many individuals have a gastrointestinal allergy to one or more foods, food additives and/or other materials and that many of these allergies are of the type 4 hypersensitivity type. Furthermore, it is believed that many of the same foods, food additives and/or other materials that are known to cause allergic contact dermatitis (type 4 hypersensitivity) of the skin are responsible for these gastrointestinal allergies, and that the allergies manifest as gastrointestinal symptoms commonly attributed to IBS.

Thus, many individuals with IBS or symptoms suggesting IBS may have a type 4 hypersensitivity to one or more foods, food additives and/or other materials which might be identifiable using skin patch testing. Skin patch tests results could be used as a basis for recommending as a treatment for the person involved that they limit consumption of the foods, food additives and/or other materials shown to cause a skin reaction for them. In this disclosure and the claims that follow, unless indicated otherwise, IBS shall be understood to refer to irritable bowel syndrome as well as other illnesses with symptoms suggestive of IBS, the latter including undifferentiated or undiagnosed gastrointestinal illness with such symptoms.

As stated above, methods and items that are useful at least therein are provided herein for IBS related testing and treatment. These may be useful in work ups for diagnosis and treatment before one or more illnesses other than IBS have been eliminated from consideration.

Accordingly, a patch for IBS related testing is provided that is attachable to skin and comprises one or more test materials, with the patch constructed such that at least one test material, selected from the group consisting of substances that can cause allergic contact dermatitis, may be brought into contact with skin to which the patch may be attached. In some embodiments, all test materials that may be brought into contact with skin to which the patch may be attached are selected from the group consisting of substances that can cause allergic contact dermatitis.

In this disclosure and the claims that follow, unless otherwise indicated, "one or more", "at least one", etc. independently mean 1,2,3, . . . up to all possible in a particular situation of what is referred to by these modifiers and should be understood to disclose each of these possibilities specifically and individually for purposes of claim support and otherwise in the situations that these modifiers are present. Expressions such as "two or more", "at least two", "three or more" and the like should be understood correspondingly. Frequently these modifiers are associated with "test material(s)" herein.

It should also be understood that in this disclosure and the claims that follow that, unless otherwise indicated, substances that "can cause allergic contact dermatitis" are substances known to do so in one or more individuals with these individual(s) so affected possibly differing (even by species) for different substances. Here "individual" may be of the human or other mammalian or avian species. It is contemplated that the methods and items consistent with the present invention may be useful as to not only humans, but also for other mammalian as well as avian species that can exhibit allergic contact dermatitis and IBS, and this disclosure and the claims that follow should be interpreted accordingly, unless otherwise indicated.

There are many substances that can cause allergic contact dermatitis currently known in the art and many more will likely be discovered in future. In addition to such substances currently known, those discovered in future (which may include diallyl mono, tri and/or tetra sulfides) are considered included in the scope of the invention and claims that follow as applicable and as allowed by applicable law. Many such substances currently known are found in the foods commonly eaten in the U.S. and other countries; these include: onion; garlic; vanillin (one source is vanilla bean extract); eugenol and isoeugenol (sources include clove and cinnamon extract); sodium benzoate (often used as a preservative; occurs naturally in cloves, apples, plums, cinnamon and cranberries for example); 2,6-di-tert-butyl-4-cresol (BHT—may be used as an antioxidant in foods and other products); menthol (may be derived from peppermint oil or produced synthetically); cinnamic alcohol (common also in perfumes and deodorants); cinnamic aldehyde (cinnamyl—commonly a flavoring in toothpaste and foods); 2-tert-butyl-4-methoxyphenol (BHA—may be used as an antioxidant in foods and other products; may cause depigmentation); anethole (an aromatic compound often found/used in essential oils, seasonings and other products); sorbic acid (commonly used as a mold and yeast inhibitor for foods, especially cheeses); benzoic acid (often a food preservative); propionic acid (often used as an herbicide, fungicide and mold inhibitor in bread and cheese products); octyl gallate (often used as an antioxidant in food products); dipentene (limonene—often a stabilizer in oils such as cardamom, mace, nutmeg, celery and caraway; also found in carrots, oranges, lemon and dill); benzoyl peroxide (often used to bleach flour, bread and other food; also an acne medication); propyl gallate (a preservative and antioxidant in many foods); dodecyl gallate (often used as an antioxidant in foods); nickel sulfate hexahydrate (trace amounts found in some foods; common component in jewelry); propylene glycol (often used as a preservative and solvent for food flavoring agents); parabens (often used as preservatives in foods); Balsam of Peru (often a flavoring in foods and drinks); sesquiterpene lactones (found in lettuce and other plants from the Compositae family; used in lotions, perfumes and other cosmetics); dl-alpha-tocopherol acetate (vitamin E; often an antioxidant in foods); wool alcohols (such as lanolin; often a chewing gum additive);

diallyl disulfide (present in garlic and possibly related vegetables); allypropyl disulfide (present in garlic and possibly related vegetables); allicin (present in garlic and possibly related vegetables); chive; leek; carrot; cucumber; horseradish; lemon peel; endive; lettuce; asparagus; artichoke; and cinnamon. For ease of reference, the 41 substances listed here may be referred to as "the group of 41 common test materials for use". Any or all of these 41 substances or various groupings of them may be used as test materials where such are called for, and any such possibilities may be used as such and are hereby specifically disclosed. Of the 41 substances here, garlic, diallyl disulfide, allypropyl disulfide and allicin among others are preferred; note that garlic is present in a very wide variety of foods and diallyl disulfide, allypropyl disulfide and allicin are present in garlic.

The sensitizing substances of many plants are present mainly in the "oleoresin fraction" which is "fat soluble." In a few plants, the allergens are water soluble glucosides or other aqueous fractions. The oleoresin fraction usually consists of a mixture of substances, which may include essential oils, terpenes, resins, phenols, and/or camphors. "Essential oils" are usually part of an oleoresin fraction and contain most of the sensitizing substances identified, and they usually occur in localized regions of the plant, such as the flower, leaf, or peel, depending on the plant.

In this disclosure and the claims that follow, recitation of onion, garlic, chive, leek, carrot, cucumber, horseradish, lemon peel, endive, lettuce, asparagus, artichoke or cinnamon should be understood to refer to any and all of their raw, cooked, dehydrated, powdered, reconstituted or like forms as applicable, unless specifically indicated otherwise, but not (other) extracts, oils or fractions such as the oleoresin ("fat soluble") fraction, essential oils or aqueous fractions, unless specifically indicated otherwise. It should be understood that this discussion provides specific and individual disclosure as test materials as applicable herein for all the separate forms mentioned here for each of onion, garlic, chive, leek, carrot, cucumber, horseradish, lemon peel, endive, lettuce, asparagus, artichoke and cinnamon; that is for the raw, cooked, dehydrated, powdered, reconstituted or like forms, as well as (other) extracts, oils or fractions such as the oleoresin ("fat soluble") fraction, essential oils or aqueous fractions of each. For ease of reference, these separate forms of onion, garlic, chive, leek, carrot, cucumber, horseradish, lemon peel, endive, lettuce, asparagus, artichoke and cinnamon shall be referred to collectively as the "vegetable forms." Specific subsets of any or all of onion, garlic, chive, leek, carrot, cucumber, horseradish, lemon peel, endive, lettuce, asparagus, artichoke and cinnamon in any or all of these separate forms as applicable are hereby disclosed as well.

It should also be understood in this disclosure and the claims that follow that the individual components recited are to be taken as non-overlapping, unless otherwise specifically indicated. For example, garlic (which contains diallyl disulfide) should not be considered to overlap with diallyl disulfide (and vice versa) in this disclosure or the claims that follow, unless overlap is otherwise specifically indicated. In addition, it should be understood that in this disclosure and the claims that follow that recitation of a carboxylic acid is understood to include the acid as well as any salt form of this acid (and vice versa) and that recitation of a specific hydrate of a substance is understood to include all other hydrates of the same substance and the anhydrous form as well.

To avoid false positives and/or erroneous results due to contaminants, test materials would ordinarily be used in at least fairly pure form and kept separate from other test materials when applied during testing. However, test materials may be mixed with solid, semi-solid, viscous or gelatinous, non-toxic, hypoallergenic materials to keep them in place (such as petrolatum for "fat soluble" test materials). In some instances, non-toxic vehicles such as water and/or acetone might be used with test materials to enhance their delivery to the skin and/or penetration thereof. Some direct mixtures of test materials might be used in some instances such as in rapid screening applications; in this disclosure, such mixtures should not be assumed, unless specifically stated. Refrigeration may be required to keep test materials in a suitable condition prior to use.

In some embodiments, patches may include at least 1,2, 3,4, . . . , or 40 test materials selected from "the group of 41 common test materials for use" or specific subsets of this group (hereby disclosed); or comprise all of "the group of 41 common test materials for use" or specific subsets of this group (hereby disclosed). The patches may sometimes only contain 1,2,3, . . . , or 41 test materials of which all are selected from "the group of 41 common test materials for use" or specific subsets of this group (hereby disclosed). The test materials of some preferred patches comprise onion, garlic and diallyl disulfide; garlic and diallyl disulfide; or diallyl disulfide, while some preferred patches have at least one test material selected from the group consisting of garlic and diallyl disulfide. Test materials in other preferred patches comprise all or at least one of diallyl disulfide, allypropyl disulfide and allicin. In still other preferred patches, test materials comprise at least one of the group consisting of an oleoresin fraction of each of the following: onion; garlic; chive; leek; carrot; cucumber; horseradish; lemon peel; endive; lettuce; asparagus; artichoke; and cinnamon. Another preferred patch has at least one test material that may be brought into contact with skin to which the patch may be attached selected from the group consisting of an oleoresin fraction of garlic, diallyl disulfide, allypropyl disulfide and allicin.

Patches may be made of plastic with chambers formed into them or have finn chambers (small metal disks that act as wells or chambers) for holding test materials, among other possibilities. Chambers may contain filter paper to help secure the test materials to the patch. Test materials may be added from syringes just before use or may come already impregnated into or otherwise inside the chambers, among other possibilities; impregnated test materials or those pre-loaded inside chambers are often preferred. Test materials may be homogenized in one or more of the following materials to produce films that can be incorporated into patches: hydroxypropyl cellulose, methylcellulose, polyvidone and beta-cyclodextrin.

Any of the patches (as singles and/or multiples at one time and/or in time series) may be used in some embodiments of the kits or methods in accordance with the present invention as applicable. It is possible that commercially available patches may be adapted as patches and/or as part of kits in accordance with the present invention and/or adapted for use in the methods in accordance with the present invention. Candidates for this adaptation may include some or all patches currently available from Dormer Laboratories, Inc., Allerderm Laboratories, Chemotechnique Diagnostics, Hermal, Mekos Laboratories, Brial Allergen GmbH, or SmartPractice Canada.

Also, a kit is provided for IBS related testing comprising information on the use of the kit or direction to such information, the information comprising indication of at least a possible link between allergic contact dermatitis or at least one material that can cause allergic contact dermatitis and IBS. The kit may further comprise at least one test material that can cause allergic contact dermatitis, at least one patch attachable to skin for use in allergic contact dermatitis testing of at least one test material, and/or a test material that can cause allergic contact dermatitis which is incorporated into a patch attachable to skin for use in allergic contact dermatitis testing of the test material.

It should be understood that "direction to such information" in the kit may include provision of a mailing address, phone number, web or online chat address, email address, or a name or logo that would bring up one of these if searched by web or directory or the like, among other possibilities, where one could obtain information on the use of the kit if one asked or made inquiry there or would be automatically given it upon contact there. Further, "indication of at least a possible link between at least one material that can cause allergic contact dermatitis and IBS" does not require that the material be identified as one that can cause allergic contact dermatitis, but just that it does so according to the criteria given in this disclosure.

In some embodiments, the kit includes at least 1,2,3, . . . or 40 test materials selected from "the group of 41 common test materials for use" or specific subsets of this group (hereby disclosed); or comprises all of "the group of 41 common test materials for use" or specific subsets of this group (hereby disclosed). The kit may sometimes only contain 1,2,3, . . . or 41 test materials of which all are selected from "the group of 41 common test materials for use" or specific subsets of this group (hereby disclosed). The test materials of some preferred embodiments of the kit comprise onion, garlic and diallyl disulfide; garlic and diallyl disulfide; or diallyl disulfide, while some preferred embodiments have at least one test material selected from the group consisting of garlic and diallyl disulfide. Test materials in other preferred kits comprise all or at least one of diallyl disulfide, allypropyl disulfide and allicin. Other preferred kits have at least one test material selected from the group consisting of an oleoresin fraction of garlic, diallyl disulfide, allypropyl disulfide and allicin.

Some preferred embodiments of the kit have at least one test material that can cause allergic contact dermatitis supplied in a medium comprising a solid, semi-solid, gelatinous or viscous, non-toxic, hypoallergenic material such as petrolatum; this non-toxic, hypoallergenic material may be useful to keep a test material in place. Some other preferred embodiments of the kit have at least one test material that can cause allergic contact dermatitis supplied in a medium comprising at least one of the group consisting of petrolatum, hydroxypropyl cellulose, methylcellulose, polyvidone, water and beta-cyclodextrin.

Any form of the kit in accordance with the present invention may be used in any method in accordance with the present invention as applicable.

A method of IBS related testing is provided comprising performing skin patch testing on a patient presenting IBS symptoms using at least one test material that can cause allergic contact dermatitis. This method of IBS related testing may include at least 1,2,3, . . . or 40 test materials selected from "the group of 41 common test materials for use" or specific subsets of this group (hereby disclosed); or comprise all of "the group of 41 common test materials for use" or specific subsets of this group (hereby disclosed). This method may sometimes only contain 1,2,3, . . . or 41 test materials of which all are selected from "the group of 41 common test materials for use" or specific subsets of this group (hereby disclosed). The test materials used in some preferred embodiments of this method comprise onion, garlic and diallyl disulfide; garlic and diallyl disulfide; or diallyl disulfide, while others have at least one test material selected from the group consisting of garlic and diallyl disulfide. Test materials in other preferred embodiments of this method comprise all or at least one of diallyl disulfide, allypropyl disulfide and allicin. In still other preferred embodiments of this method, at least one test material is selected from the group consisting of an oleoresin fraction of garlic, diallyl disulfide, allypropyl disulfide and allicin.

In some preferred embodiments of this method in accordance with the present invention, at least one test material that can cause allergic contact dermatitis is used that is supplied in a medium comprising a solid, semi-solid, gelatinous or viscous, non-toxic, hypoallergenic material such as petrolatum; this material may be useful to keep a test material in place. Some other preferred embodiments of this method involve having at least one test material that can cause allergic contact dermatitis supplied in a medium comprising at least one of the group consisting of petrolatum, hydroxypropyl cellulose, methylcellulose, polyvidone and beta-cyclodextrin.

This method of IBS related testing may further comprise limiting the intake by the patient of at least 1,2,3, . . . material(s) that give(s) a positive skin patch test result in the patient, and in some embodiments, at least 1,2,3, . . . , 41 material(s) limited may be selected from the group consisting of "the group of 41 common test materials for use" or specific subsets of this group (hereby disclosed), or the limited materials may be from the group consisting of onion, garlic and diallyl disulfide, or the group consisting of garlic and diallyl disulfide, or diallyl disulfide, while other embodiments have at least one limited material selected from the group consisting of garlic and diallyl disulfide, and in still others, limited materials comprise all or at least one of diallyl disulfide, allypropyl disulfide and allicin; or at least one of the materials limited is garlic.

A method of treatment of IBS is provided comprising limiting the intake by a patient presenting IBS symptoms of at least 1,2,3, . . . material(s) that give(s) a positive skin patch test result in the patient, and in some embodiments, at least 1,2,3, . . . , or 41 material(s) limited may be selected from the group consisting of "the group of 41 common test materials for use" or specific subsets of this group (hereby disclosed) or the limited materials may be from the group consisting of onion, garlic and diallyl disulfide, or the group consisting of garlic and diallyl disulfide, or diallyl disulfide, while some embodiments have at least one limited material selected from the group consisting of garlic and diallyl disulfide, and in still others, limited materials comprise all or at least one of diallyl disulfide, allypropyl disulfide and allicin; or at least one of the materials limited is garlic.

The following examples should be taken as illustrative, but should not be interpreted so as to unnecessarily limit the scope of the disclosure herein or the claims that follow.

Example 1

Two types of patients participated: (1) patients with a known history of irritable bowel syndrome (IBS) or symptoms suggestive of IBS (symptomatic patients) and (2) patients with no gastrointestinal issues as control (asymptomatic patients).

Criteria for symptomatic patients used for purposes of this example were: abdominal pain and discomfort lasting at least 12 weeks in a 12 month period, though the weeks did not have to occur consecutively and at least two of the following:

(1) A change in the frequency or consistency of stool;
(2) Straining, urgency or a feeling of incomplete emptying of the bowels;
(3) Mucus in the stool; and
(4) Bloating or abdominal distension.

Two patches were applied to the skin of each patient, one containing raw garlic and one containing raw onion. The patches were left in place for 48 hours, and then removed. Readings of the patch test sites were performed immediately at 48 hours after application and again 24 or 48 hours after that—72 or 96 hours after application. It was found that 11 of 21 symptomatic patients (52.4%) had a positive patch test reaction to garlic and 2 of 21 (9.5%) had a positive patch test to onion; 3 of 12 asymptomatic (control) patients (25.0%) had a positive patch test to garlic as did 3 of 12 (25.0%) to onion. Garlic appears to be more relevant than onion for IBS, at least in the patients tested here. A skin biopsy from a positive patch test site to garlic in one symptomatic patient showed findings typical of allergic contact dermatitis (type 4 hypersensitivity). Of the 11 symptomatic patients that had a positive patch test for garlic, 10 tried a garlic free diet for 3 to 7 days; of the latter, 4 reported no improvement, 2 reported slight improvement, 3 reported moderate improvement and 1 reported marked improvement in gastrointestinal symptoms.

Example 2

Following the same basic procedure as in Example 1, but this time using the first 28 of "the group of 41 common test materials for use," the following results were obtained. In the 6 control (asymptomatic) patients, all patch tests were negative. In the 15 symptomatic patients (with IBS or IBS-like symptoms), 6 of the 15 had one positive patch test (2 for garlic; 1 for dipentene; 1 for nickel sulfate; 1 for benzoyl peroxide; and 1 for dodecyl gallate). Of the 6 symptomatic patients who had a positive patch test, 4 completed a 1 week avoidance diet for their respective positive test material with 2 reporting much improvement, 1 reporting moderate improvement and 1 reporting slight improvement.

Example 3 (Prophetic)

Skin patch testing may be performed using "the group of 41 common test materials for use" (which are common food and food additive allergens known to cause allergic contact dermatitis (type 4 hypersensitivity)) on patients with known self-reported history of gastrointestinal intolerance to garlic and/or onions and/or on individuals with physician-diagnosed IBS or symptoms suggestive of IBS. As a control, the same tests may be performed on individuals with no history of food intolerance, IBS or symptoms suggestive of IBS. Patients from the non-control group with one or more positive patch tests may be placed on a diet for 1 week, avoiding the food/food additive allergens to which they have tested positively to determine whether avoidance of the suspect allergen(s) alleviates their gastrointestinal symptoms.

Participants should usually be at least 18 years of age. Other exclusion criteria are taking any cortisone-containing medicine by injection or by mouth during the study or in the week preceding the study, pregnancy, a severe rash, or known severe allergy to garlic, onions, adhesive tape, or any of the other allergens to be used in this protocol.

Other than onion and garlic, patch test allergens used in the testing may not be currently available in the U.S., but they may be supplied by Dormer Laboratories, Inc. of Canada and manufactured by Chemotechnique Diagnostics of Sweden.

After obtaining informed consent, in one implementation, a method is as follows:

Day 1: Small pieces of garlic and onion and the 39 other common food and food additive allergens from "the group of 41 common test materials for use", the latter 39 mixed with petrolatum, are placed in small inert polyethylene plastic chambers and taped with hypoallergenic non-woven adhesive tape to the upper back. The patient is instructed to keep the upper back dry until the Day 3 visit (2 days after the tests are placed). Swimming and excessive sweating should be avoided for these 2 days to assure the tape remains secure and the patch tests remain in place.

Day 3: The tape and chambers containing the food and food additive allergens are removed and the first patch test reading is recorded. Readings may be performed by one non-blinded and one blinded investigator. The blinded investigator is unaware of the participant's questionnaire answers and gastrointestinal status. The sites will be marked with a non-permanent magic marker. From this point and beyond, the patient may shower normally except to avoid soaping and scrubbing the upper back so the magic marker markings are not washed off until after the third (final) visit.

Day 4 or 5: The patch test sites are read by the non-blinded and blinded investigator for the final time.

Photographic documentation of positive patch tests reactions may be recorded. Any symptomatic study patients who have one or more positive patch tests are given information sheets for the allergens to which they test positively and asked to avoid these allergens for one full week. A brief follow-up questionnaire may be distributed as well, inquiring about the outcome of the avoidance diet.

The foregoing description of various embodiments provides illustration and description, but is not intended to be exhaustive or to limit the invention to the precise form disclosed. Modifications and variations are possible in light of the above teachings or may be acquired from practice in accordance with the present invention. It is to be understood that the invention is intended to cover various modifications and equivalent arrangements included within the spirit and scope of the appended claims.

What is claimed is:

1. A method of identifying allergens that cause irritable bowel syndrome (IBS) in a patient using a relation between Type 4 allergic contact dermatitis and IBS, comprising:
   selecting a patient having one of: (1) a history of IBS and (2) symptoms of IBS;
   applying, to skin of the patient, a patch comprising one or more test materials selected from the group consisting of food and food based additive substances that are known to cause Type 4 allergic contact dermatitis, wherein the patch is configured to be attached to skin such that the one or more test materials is brought into contact with skin to which the patch is attached;
   determining whether a positive Type 4 allergic contact dermatitis reaction has occurred on the skin of the patient; and
   limiting the intake by the patient of at least one material that gives the positive Type 4 allergic contact dermatitis reaction to determine whether the one or more test materials cause IBS in the patient.

2. The method of claim 1 wherein at least one test material is selected from the group consisting of onion; garlic; vanillin; eugenol; isoeugenol; sodium benzoate; 2,6-di-tert-butyl-4-cresol; menthol; cinnamic alcohol; cinnamic aldehyde; 2-tert- butyl-4- methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru; sesquiterpene lactones; dl- alpha-tocopherol acetate; wool alcohols; diallyl disulfide; allypropyl disulfide; allicin; chive; leek; carrot; cucumber; horseradish; limonene; endive; lettuce; asparagus; artichoke; and cinnamon.

3. The method of claim 1 wherein at least one test material is selected from the group consisting of vanillin; eugenol; isoeugenol; sodium benzoate; 2,6-di-tert- butyl-4- cresol; menthol; cinnamic alcohol; cinnamic aldehyde; 2-tert-butyl-4- methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru; sesquiterpene lactones; dl-alpha-tocopherol acetate; wool alcohols; diallyl disulfide; allypropyl disulfide; and allicin.

4. The method of claim 1 wherein at least one test material is selected from the group consisting of an oleoresin fraction of garlic, diallyl disulfide, allypropyl disulfide and allicin.

5. The method of claim 1 wherein at least one of the materials limited is selected from the group consisting of onion; garlic; vanillin; eugenol; isoeugenol; sodium benzoate; 2,6-di-tert-butyl-4-cresol; menthol; cinnamic alcohol; cinnamic aldehyde; 2-tert- butyl-4-methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru; sesquiterpene lactones; dl-alpha-tocopherol acetate; wool alcohols; diallyl disulfide; allypropyl disulfide; allicin; chive; leek; carrot; cucumber; horseradish; limonene; endive; lettuce; asparagus; artichoke; and cinnamon.

6. The method of claim 1 wherein at least one of the materials limited is selected from the group consisting of vanillin; eugenol; isoeugenol; sodium benzoate; 2,6-di-tert-butyl-4-cresol; menthol; cinnamic alcohol; cinnamic aldehyde; 2-tert- butyl-4- methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru;
sesquiterpene lactones; dl-alpha-tocopherol acetate; wool alcohols; diallyl disulfide;
allypropyl disulfide; and allicin.

7. The method of claim 1 wherein at least one of the materials limited is garlic.

8. The method of claim 1, comprising applying, to skin of the patient, a patch comprising 28 or more test materials.

9. The method of claim 1, comprising applying, to the skin of the patient, a patch comprising 40 or more test materials.

10. A method of treating IBS in a patient, comprising:
selecting a patient having one of: (1) a history of IBS and (2) symptoms of IBS;
applying, to skin of the patient, a patch comprising one or more test materials selected from the group consisting of food and food based additive substances that are known to cause Type 4 allergic contact dermatitis, wherein the patch is configured to be attached to skin such that the one or more test materials is brought into contact with skin to which the patch is attached;
determining whether a positive Type 4 allergic contact dermatitis reaction has occurred on the skin of the patient; and
limiting the intake by the patient of at least one material that gives the positive Type 4 allergic contact dermatitis reaction to treat the IBS in the patient.

11. The method of claim 10 wherein at least one test material is selected from the group consisting of onion; garlic; vanillin; eugenol; isoeugenol; sodium benzoate; 2,6-di-tert-butyl-4-cresol; menthol; cinnamic alcohol; cinnamic aldehyde; 2-tert- butyl-4- methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru; sesquiterpene lactones; dl- alpha-tocopherol acetate; wool alcohols; diallyl disulfide; allypropyl disulfide; allicin; chive; leek; carrot; cucumber; horseradish; limonene; endive; lettuce; asparagus; artichoke; and cinnamon.

12. The method of claim 10 wherein at least one test material is selected from the group consisting of vanillin; eugenol; isoeugenol; sodium benzoate; 2,6-di-tert- butyl-4-cresol; menthol; cinnamic alcohol; cinnamic aldehyde; 2-tert-butyl-4- methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru; sesquiterpene lactones; dl-alpha-tocopherol acetate; wool alcohols; diallyl disulfide; allypropyl disulfide; and allicin.

13. The method of claim 10 wherein at least one test material is selected from the group consisting of an oleoresin fraction of garlic, diallyl disulfide, allypropyl disulfide and allicin.

14. The method of claim 10 wherein at least one of the materials limited is selected from the group consisting of onion; garlic; vanillin; eugenol; isoeugenol; sodium benzoate; 2,6-di-tert-butyl-4-cresol; menthol; cinnamic alcohol; cinnamic aldehyde; 2-tert- butyl-4-methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru; sesquiterpene lactones; dl-alpha-tocopherol acetate; wool alcohols; diallyl disulfide; allypropyl disulfide; allicin; chive; leek; carrot; cucumber; horseradish; limonene; endive; lettuce; asparagus; artichoke; and cinnamon.

15. The method of claim 10 wherein at least one of the materials limited is selected from the group consisting of vanillin; eugenol; isoeugenol; sodium benzoate; 2,6-di-tert-butyl-4-cresol; menthol; cinnamic alcohol; cinnamic aldehyde; 2-tert- butyl-4- methoxyphenol; anethole; sorbic acid; benzoic acid; propionic acid; octyl gallate; dipentene; benzoyl peroxide; propyl gallate; dodecyl gallate; nickel sulfate hexahydrate; propylene glycol; parabens; Balsam of Peru; sesquiterpene lactones; dl-alpha-tocopherol acetate; wool alcohols; diallyl disulfide; allypropyl disulfide; and allicin.

16. The method of claim 10 wherein at least one of the materials limited is garlic.

17. The method of claim 10, comprising applying, to skin of the patient, a patch comprising 28 or more test materials.

18. The method of claim 10, comprising applying, to the skin of the patient, a patch comprising 40 or more test materials.

* * * * *